United States Patent
Chappell et al.

(10) Patent No.: US 9,757,047 B2
(45) Date of Patent: Sep. 12, 2017

(54) FAST ANALYSIS METHOD FOR NON-INVASIVE IMAGING OF BLOOD FLOW USING VESSEL-ENCODED ARTERIAL SPIN LABELLING

(71) Applicant: Isis Innovation Ltd., Oxford (GB)

(72) Inventors: Michael Chappell, Oxford (GB); Mark Woolrich, Oxford (GB); Thomas Okell, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 1162 days.

(21) Appl. No.: 13/815,815

(22) Filed: Mar. 14, 2013

(65) Prior Publication Data

US 2013/0249547 A1 Sep. 26, 2013

Related U.S. Application Data

(60) Provisional application No. 61/685,599, filed on Mar. 20, 2012.

(51) Int. Cl.
| | | |
|---|---|---|
| *G01V 3/00* | (2006.01) | |
| *A61B 5/026* | (2006.01) | |
| *G01R 33/563* | (2006.01) | |

(52) U.S. Cl.
CPC ...... *A61B 5/0263* (2013.01); *G01R 33/56333* (2013.01); *G01R 33/56366* (2013.01)

(58) Field of Classification Search
CPC .............................................. G01R 33/56333
USPC ................................................ 324/306, 309
See application file for complete search history.

(56) References Cited

U.S. PATENT DOCUMENTS

| | | | | |
|---|---|---|---|---|
| 2008/0269595 | A1* | 10/2008 | Wong | A61B 5/055 600/411 |
| 2012/0271157 | A1* | 10/2012 | Wong | A61B 5/055 600/419 |
| 2013/0253895 | A1* | 9/2013 | Okell | A61B 6/507 703/11 |
| 2014/0235994 | A1* | 8/2014 | Jezzard | A61B 5/055 600/410 |
| 2015/0297101 | A1* | 10/2015 | Hernandez-Garcia | G01R 33/56563 600/419 |
| 2016/0296126 | A1* | 10/2016 | Berry | A61B 5/0263 |

* cited by examiner

*Primary Examiner* — Louis Arana
(74) *Attorney, Agent, or Firm* — Thomas | Horstemeyer, LLP (57) ABSTRACT

Arterial spin labelling (ASL) MRI offers a non-invasive means to create blood-borne contrast in vivo for dynamic angiographic imaging. By spatial modulation of the ASL process it is possible to uniquely label individual arteries over a series of measurements, allowing each to be separately identified in the resulting images. This separation requires appropriate analysis for which a general framework has previously been proposed. Here the general framework is modified for fast analysis of non-invasive imaging of blood flow using vessel encoded arterial spin labelling (VE-ASL). This specifically addresses the issues of computational speed of the analysis and the robustness required to deal with real patient data. The modification applies various approaches for estimation of one or more parameters that change the way a vessel, for example an artery, is encoded to provide the fast analysis.

20 Claims, 8 Drawing Sheets

FAST ANALYSIS METHOD FOR NON-INVASIVE IMAGING OF BLOOD FLOW USING VESSEL-ENCODED ARTERIAL SPIN LABELLING

CROSS REFERENCE TO RELATED APPLICATIONS

This application claims priority to U.S. provisional application entitled "A FAST ANALYSIS METHOD FOR NON-INVASIVE IMAGING OF BLOOD FLOW USING VESSEL-ENCODED ARTERIAL SPIN LABELLING" having Ser. No. 61/685,599, filed Mar. 20, 2012, which is hereby incorporated by reference in its entirety.

INCORPORATION BY REFERENCE

Applicant incorporates by reference the following publications as if they were fully set forth herein expressly in their entireties:
1) Chappell, M. A., Okell, T. W., Jezzard, P., Woolrich, M. W., 2010. A General Framework for the Analysis of Vessel Encoded Arterial Spin Labelling for Vascular Territory Mapping. Magnetic Resonance in Medicine 64, 1529-1539.
2) Okell, T. W., Chappell, M. A., Woolrich, M. W., Guenther, M., Feinberg, D. A., Jezzard, P., 2010. Vessel-Encoded Dynamic Magnetic Resonance Angiography Using Arterial Spin Labelling. Magnetic Resonance in Medicine 64, 698-706.
3) Each and every one of the rest of the publications listed in the References section appended hereto.

TECHNICAL FIELD

The present disclosure generally relates to medical imaging and more particularly, relates to systems and methods for providing clinicians with quantitative blood flow rate information to help make diagnostic, prognostic or therapeutic decisions.

BACKGROUND

Arterial spin labelling (ASL) magnetic resonance imaging (MRI) is an entirely non-invasive means to measure blood flow in the body, for example as the supply of blood to the tissues (perfusion) or to visualize blood flow within arteries (angiography). In ASL an endogenous 'contrast agent' is generated by radio-frequency inversion of the magnetization of flowing blood upstream from the organ being investigated, followed by subsequent imaging of this labelled blood once it has reached the organ. An example is labelling blood in the neck to measure blood flow in the brain. This image is subtracted from another taken in the absence of labelling to remove the static tissue signal and reveal the blood supply, from which quantitative measures of blood flow can be derived (Alsop and Detre, 1996; Buxton et al., 1998). The ASL contrast mechanism can also be applied to angiographic imaging of the vessels, including dynamic ('cine') acquisitions (Edelman et al., 1994; Wang et al., 1991).

Some organs, most notably the brain, are supplied with blood by a number of arteries, each artery supplying a different region; commonly referred to as vascular territories. It is of clinical relevance to be able to visualise the blood flow within individual arteries and the territories they supply. A notable example is collateral flow in the 'Circle of Willis' whereby blood may pass from one major artery via a communicating artery to feed a different vascular territory. For example, flow from an internal carotid artery may be diverted to a posterior territory normally supplied by the vertebral arteries in the case of vertebral occlusion or stenosis. A number of selective ASL labelling methods have been proposed that can target individual arteries (Helle et al., 2010a; Helle et al., 2010b) (Dai et al., 2010) (Davies and Jezzard, 2003) (Zimine et al., 2006) (Hendrikse et al., 2004).

Recently a more efficient strategy has been demonstrated for the simultaneous labelling of multiple arteries (Gunther, 2006) (Wong, 2007), termed vessel-encoded ASL (VE-ASL). This method can be used to produce vessel-selective dynamic angiograms of the major cerebral arteries (Okell et al., 2010). Vessel encoded ASL extends the ASL concept to the unique labelling of the arteries so their individual contributions can be visualized and quantified. This is achieved by modulation of the labelling profile over a series of image acquisitions. The blood in the different arteries ends up being uniquely encoded in the data. We might say it has been barcoded. The method is relatively efficient, since in every cycle of the acquisition multiple arteries are labelled (albeit to differing degrees). This is in contrast to methods where individual arteries are targeted one at a time.

Figure 1:
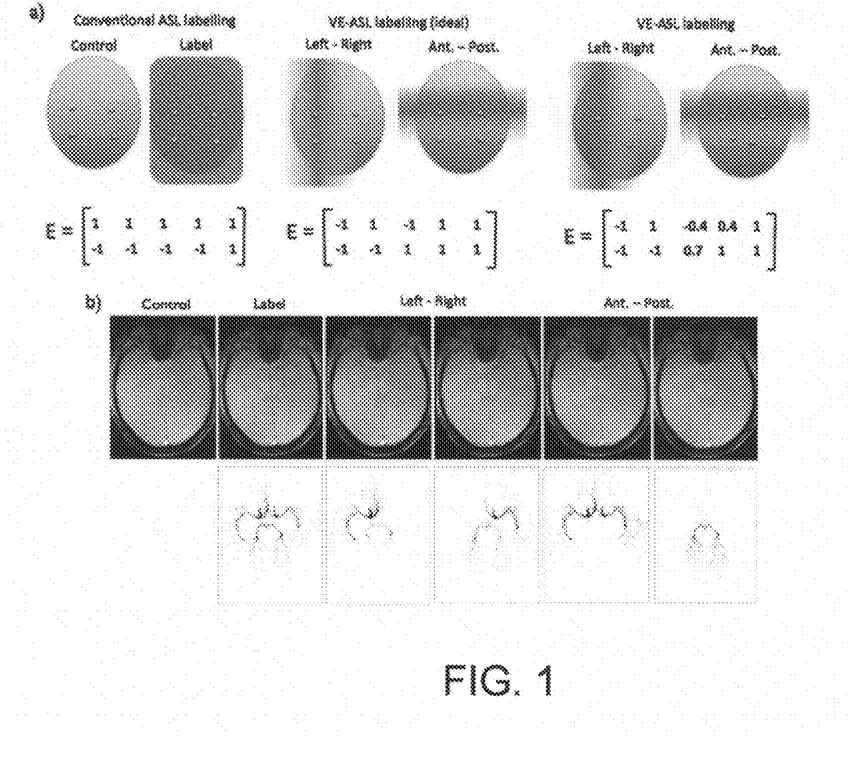
FIG. 1 depicts a guide to VE-ASL dynamic angiography: a) labelling in the neck and the associated encoding matrix for four arteries (right and left internal carotids, right and left vertebrals) plus static tissue contribution; and b) example VE-ASL angiographic images in the brain showing raw image (dominated by static tissue contribution) and result after subtraction from the control image.

An example of VE-ASL imaging is given in FIG. 1. Conventional ASL fully inverts the blood in all arteries within the labelling regions. Subtraction of the subsequent image from a control, in the absence of labelling, produces an image of flowing blood. VE-ASL spatially modulates the inversion process such that in one acquisition within a subset of arteries the blood will be inverted and the remainder will remain in the unlabelled (control) condition. Over a number of such acquisitions, with different modulations, each artery will have been uniquely encoded and its contribution to the blood flow image can be extracted in post-processing. Complications arise, however, because it is necessary to use post-processing to separate the different artery contributions.

The most straightforward approach to post-processing such data involves simple addition or subtraction of images (typically written as the equivalent matrix operation). However, more complex encodings and imperfections in the modulation, for example due to non-ideal locations of the arteries within the labelling region, necessitate more careful analysis (Chappell et al., 2010; Wong et al., 2006). This typically involves the specification of the mixing or encoding matrix (FIG. 1) for the different artery contributions under the encoding cycles employed in the acquisition. The (Moore-Penrose) pseudo-inverse of this matrix can then be used in post-processing to calculate individual artery contributions to the flow.

We previously proposed a general framework for the analysis of VE-ASL data employing a Bayesian solution (Chappell et al., 2010). It offered a number of advantages over existing matrix inversion approaches. In particular, it provided a full model for the relationship between the locations of the arteries in the labelling plane and the encoding profile, allowing the locations to be inferred from the data whilst permitting prior information from planning acquisitions to be incorporated. Furthermore, a voxel-wise classification with N-arteries per class was used to restrict the number of arteries that were assumed to contribute to the signal in a voxel, resulting in greater signal-to-noise ratio (SNR) efficiency and reductions in the number of encoding cycles required.

The general framework was demonstrated on VE-ASL imaging of the cerebral vascular territories (Chappell et al., 2010). However, a number of limitations were present in the existing framework that become more acute in the case of angiographic data, particularly when coupled with clinical application. First, the original proposal employs a Markov Chain Monte Carlo (MCMC) sampling procedure to infer the 'global' parameters, e.g. the artery locations in the labelling region or region of interest (ROI). This results in a relatively long computation time, something that will be more pronounced in higher resolution angiographic data. Second, while there are potential benefits in fully inferring the artery locations from the data, in a clinical setting it may be more beneficial to constrain the artery locations based on information obtained in the planning phase and according to variation that might be expected due to patient movement, for example, constraining the artery locations by only permitting a global three degree-of-freedom transformation. This will result in fewer parameters in the analysis and so should be more robust to the poorer signal-to-noise ratio (SNR) and greater frequency of motion artefacts expected of clinical data, which is caused by greater decay of the ASL label during the delayed blood transit, typical of patients with cerebrovascular disease. Additionally, in patients with highly stenosed arteries that provide little signal downstream, allowing completely free determination of the artery locations leaves the analysis vulnerable to bias by artefacts and incorrect assignment of the signal components. In these cases it may sometimes be critical to differentiate between low flow and zero flow, so a method that is robust to small signals from some arteries is desirable.

Accordingly, there is a need to address the aforementioned deficiencies and inadequacies.

SUMMARY

Disclosed herein are systems and methods for modifying the aforementioned existing general framework for vessel encoded arterial spin labelling (VE-ASL) analysis that address the issues arising from its use. The general framework is modified for fast analysis of blood flow imaging. The present modification can apply to both perfusion as well as angiography and is particularly suited for determining blood flow contributions from individual cerebral arteries. It specifically addresses the issues of computational speed of the analysis and the robustness required to deal with real patient data. The modification applies an estimation of one or more parameters, sometimes referred to as global parameters, that change the way a vessel, for example an artery, is encoded to provide the fast analysis.

Briefly described in various aspects a method is provided for non-invasive imaging of blood flow using vessel-encoded arterial spin labelling (VE-ASL) comprising the steps of:

A. Obtaining or acquiring data for a region of interest in a subject;
B. Estimating, in view of the data obtained, one or more parameters that describe an encoding within a labelling region of one or more vessels that supply the region of interest in the subject;
C. Acquiring vessel-encoded arterial spin labelling (VE-ASL) data for the one or more vessels in the region of interest; and
D. Applying the estimation of the one or more parameters for the analysis of the VE-ASL data to provide an image of blood flow in the region of interest that identifies the individual contributions from the vessels in the labelling region.

We may further determine from the blood flow in the one or more vessels within the region of interest an estimate of the flow contributions from those vessels to a selected voxel of interest. This may provide a voxel-wise estimate of flow contributions from each of the vessels within the region of interest.

In one or more aspects, the data obtained for a region of interest may be obtained by any one or more acquisition methods. For example, we may obtain the data by one or more planning process acquisitions. A planning process acquisition may be used in planning a subsequent VE-ASL acquisition. We may conduct a planning acquisition, or we may use data from a previously conducted acquisition. A planning process acquisition may involve use of a magnetic resonance imaging (MRI) device, positioning the subject in association with the MRI device and using the MRI device to obtain or acquire the data. In one or more aspects the estimation of the one or more parameters may be made from data from a planning process acquisition. In various aspects we may use a time-of-flight (TOF) angiography sequence, which shows the major vessels such as arteries, as a planning acquisition to localise the vessels or arteries before performing the vessel-encoded scan to acquire the VE-ASL data. These vessel locations may then be used as priors for the analysis. Other angiographic images may also be used, such as phase-contrast angiography. The data obtained may be re-used in the analysis of the VE-ASL data. The data obtained may include vessel locations, speed of blood flow, off-resonance effects within the modulation function of the MRI device and/or vessel class proportions.

In one or more aspects, the one or more parameters are estimated from the anatomy of the subject. The subject may be any animal having blood flow. For example, the subject may be a mammalian subject, including in particular a human subject such as a patient. In another embodiment, we use the MRI device to obtain a planning process acquisition of data and estimate the one or more parameters from the data obtained from the planning process. In an embodiment, the one or more parameters are a global set of estimated vessel locations, such as locations of arteries, in the region of interest. We can apply estimates of the set of global parameters derived from the planning process without further estimation. This embodiment offers an alternative to matrix inversion analyses with very minimal increase in computational cost.

In a further aspects, the one or more parameters represent a relationship between the true vessel locations and the vessel locations estimated from a planning acquisition, thus defining a new set of estimated parameters that relate, for example, the true vessel locations to the locations previously estimated. The estimation of a parameterised transformation between previously estimated vessel locations (e.g. from a planning process image) and the actual locations that generate the VE-ASL images can also provide for fast analysis of the data This can introduce constraints into the inference of global parameters, such as artery locations, that match those that might be expected from subject movement.

In a one or more further aspects, we may estimate the one or more parameters by marginalizing a posterior distribution of VE-ASL data within a region of interest to derive point estimates of the location of the one or more blood vessels within the labelling region. For example, we can employ a Maximum A Posteriori (MAP) solution for estimating 'global' parameters, such as vessel locations, to address issues of computation time, among other approaches. The image may be output to a user for analysis, or for example displayed on a monitor or other display device or printed.

The present systems and methods are equally applicable to all VE-ASL acquisitions including, for example, both dynamic angiography, and perfusion ASL. Moreover, the one or more parameters that can be estimated for fast analysis include not only vessel locations, but any parameter that changes the way each vessel is labelled or encoded. For example, the one or more parameters sometimes referred to as the "global" parameters can also include, speed of flow, off resonance effects within the modulation function, and/or class proportions.

Other systems, methods, features, and advantages of the present disclosure for providing a fast analysis method for non-invasive imaging of blood flow using vessel-encoded arterial spin labelling angiography will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Having summarized various aspects of the present disclosure, reference will now be made in detail to the description of the disclosure as illustrated in the drawings. While the disclosure will be described in connection with these drawings, there is no intent to limit it to the embodiment or embodiments disclosed herein. On the contrary, the intent is to cover all alternatives, modifications and equivalents included within the spirit and scope of the disclosure as defined by the appended claims.

The full theory for a general framework for VE-ASL data analysis is given in (Chappell et al., 2010), which is incorporated by reference as if fully set forth herein. A summary of the key ideas and equations of the analysis is given here. In conventional arterial spin labelling (ASL) all the arteries are either in the control or labelled condition. In vessel-encoded arterial spin labelling (VE-ASL) the labelling is modulated to put a subset in control whilst the others are labelled. Ideally arteries will be either fully labelled or controlled, but in practice it may not be possible to achieve this and in some acquisitions arteries will be partially labelled.

Encoding Matrix Representation

The tag-control differencing of VE-ASL can be represented in matrix form (Wong, 2007):

$$s = Ef \quad (1)$$

where f represents the sources of signal, s is the vector of (noise-less) measured values and E is the encoding matrix:

$$E = \begin{bmatrix} m_{11} & \cdots & m_{1M} & 1 \\ \vdots & \ddots & \vdots & \vdots \\ m_{N1} & \cdots & m_{NM} & 1 \end{bmatrix} \quad (2)$$

where N encoding cycles produce N images by spatially encoding the signal from M arteries. A conventional control-all image in cycle i would be generated by setting $m_{ij}=1$ for each vessel, j, and likewise for a tag-all image by setting $m_{ij}=-1$. The final column must always be all unity values, since this dictates the contribution of the static magnetization of the tissues to the measured signal. Example encoding matrices for labelling arteries in the neck are shown in FIG. 1a. FIG. 1b depicts exemplary VE-ASL angiographic images in the brain showing the raw image dominated by static tissue contribution and the result after subtraction from the control image.

N-Artery Classification

The full encoding matrix permits any voxel to receive contribution from all supply arteries. However, this is unlikely in practice since most tissue will be fed by only a subset of the labelled arteries. Analysis should ideally be performed only with a subsection of the encoding matrix representing the appropriate arteries, leading to a better-conditioned encoding matrix and more robust analysis. This can be achieved by including classification within the analysis, where each voxel is assigned a class, each class specifying a unique subset of the supply arteries. This can be described for the cth class using a matrix, $P_c$, in the kth voxel:

$$s_{k,c} = E P_c f_{k,c} \quad (3)$$

If we are considering $L_c$ arteries in the cth class, then $f_{k,c}$ will be $(L_c+1) \times 1$ in size. $P_c$ will be a matrix of zeros, $(M+1) \times (L_c+1)$ in size, with a single unity entry in each column that selects individual vessels included in this class (plus the static magnetization in the final column). For example, for a 3-artery problem (M=3), considering pairs of arteries ($L_c=2$) the $P_c$ matrices for all classes (combination of arteries) are:

$$P_c = \left\{ \begin{bmatrix} 1 & 0 & 0 \\ 0 & 1 & 0 \\ 0 & 0 & 0 \\ 0 & 0 & 1 \end{bmatrix}, \begin{bmatrix} 1 & 0 & 0 \\ 0 & 0 & 0 \\ 0 & 1 & 0 \\ 0 & 0 & 1 \end{bmatrix}, \begin{bmatrix} 0 & 0 & 0 \\ 1 & 0 & 0 \\ 0 & 1 & 0 \\ 0 & 0 & 1 \end{bmatrix} \right\}, \quad (4)$$

In essence the P matrices mean that only a section of the encoding matrix is considered at a time.

Bayesian Framework

The estimation of voxelwise class membership and flow contributions can be cast within, for example, a Bayesian framework. Assuming white noise the Likelihood, as in (Chappell et al., 2010), is given by:

$$Pr(T \mid F, E, q = \kappa, \phi) = \prod_k Pr(t_k \mid f_k, E, q_k = \kappa_k, \phi_k), \quad (5)$$

$$Pr(t_k \mid F_k, E, q_k = \kappa_k, \phi_k) = \frac{\phi_k^{N/2}}{(2\pi)^{N/2}} e^{-\frac{\phi_k}{2}(t_k - s_{k,\kappa_k})^T (t_k - s_{k,\kappa_k})}, \quad (6)$$

$$t_k = s_{k,\kappa_k}(t) + e_k(t) \quad (7)$$

$$e_k(t) \sim \prod N(0, \phi_k^{-1}) \quad (8)$$

where k refers to an individual voxel, $t_k$ is the measured data containing N measurements, q is the map of discrete class labels and κ is a specific configuration thereof, thus $\kappa_k$ is a specific class label assigned to voxel k, ϕ is the vector of noise precisions.

Application of Bayes' theorem gives the posterior distribution:

$$Pr(F,E,q=\kappa,\phi \mid T) \propto Pr(T \mid F,E,q=\kappa,\phi)Pr(F,\phi)Pr(E)Pr(q=\kappa), \quad (9)$$

with the following priors:

$$Pr(F, \phi) = \phi^{\frac{L_c}{2}} \mid P_c^T E^T E P_c^T \mid^{1/2} \quad (10)$$

$$Pr(q_k = c \mid \pi_c) = \pi_c$$

$$\sum_c \pi_c = 1$$

$$Pr(\pi_c) = 1/|\pi_c|$$

The prior on the precisions and flow estimates is the joint Jeffrey's prior for both (Lee, 1997), making the prior uninformative for these parameters. The prior probability for a voxel belonging to class c is set to be the proportion of voxels belonging to that class, $\pi_c$, as determined from the data. The prior specification includes the requirement that the class proportions must sum to unity. Additionally an automatic relevancy determination (ARD) prior is placed on each class proportion so that where data does not support that class it will be automatically removed from the model (Mackay, 1995). Finally a prior needs to be set for the encoding matrix; ideally the full encoding matrix is defined a priori by the acquisition and from the planning angiographic image at the labelling region (see below), in which case Pr(E)=1. The encoding matrix may be further parameterised, for example in terms of the locations of the arteries in the labelling plane. The encoding matrix parameters being inferred from the data and subject to prior information defined within the Pr(E) term.

Marginalization can be performed analytically over all the parameters that vary from voxel to voxel: flow, noise precision and class label in every voxel. This gives:

$$Pr(E, \pi \mid Y) \propto \prod_k \left[ E_c \left\{ \pi_c \left[ (y_k - EP_c(P_c^T E^T E P_c)^{-1} P_c^T E^T y_k)^T (y_k - EP_c(P_c^T E^T E P_c)^{-1} P_c^T E^T y_k) \right]^{\frac{N}{2}} \right\} \right] \prod_c \frac{1}{|\pi_c|} Pr(E). \quad (11)$$

Thus the voxelwise parameters do not need to be included within a numerical optimization for the parameter values, substantially reducing the computational complexity. If the encoding matrix and the class proportions are known (or estimated using equation (11)) then the flow can be calculated:

$$f_k = E(f_k \mid y_k) = \Sigma_c Pr(q_k = c \mid y_k, E, \pi_c) P_c (P_c^T E^T E P_c)^{-1} P_c^T E^T y_k \quad (12)$$

where the class posterior probabilities are calculated from:

$$Pr(q_k = c \mid y_k, E, \pi_c) = \frac{p_{k,c}}{\Sigma_c p_{k,c}} \quad (13)$$

where $p_{k,c}$ is the non-normalized class label posterior probability:

$$p_{k,c} = \pi_c \left[ (y_k - EP_c(P_c^T E^T E P_c)^{-1} P_c^T E^T y_k)^T (y_k - EP_c(P_c^T E^T E P_c)^{-1} P_c^T E^T y_k) \right]^{\frac{N}{2}}. \quad (14)$$

Encoding Matrix Entries

The encoding matrix, in equation (2), represents the combination of the applied encoding profile and the locations of the arteries within the labelling plane. In a general artery encoding scheme a number of encoded images will be acquired. Hence there will be a modulation value, m, for each combination of artery and modulation phase, i.e. for the ith encoded image and jth vessel:

$$m_{i,j} = g(x_j, v_j, c_i, \theta_i, D_i), \quad (15)$$

where g is the 1-dimensional modulation function, $x_j$ is the location and $v_j$ is the speed of flow in the jth artery, $c_i$, $\theta_i$ and $D_i$ are the centre, direction and scale of the i th encoding. The modulation function can be simulated, for example, by numerical evaluation of the Bloch equations for a range of mean flow speeds assuming a parabolic flow profile (Chappell et al., 2010; Wong, 2007). The modulation function is periodic and can be parameterized in terms of a non-dimensional phase ϕ, which can be evaluated for any combination of artery location and encoding setup from ϕ=πd/2D, where:

$$d = \begin{cases} \text{sign}(x-c_x)\sqrt{(x-c_x)^2+(y-c_y)^2} \\ \cos\left(\theta-\arctan\left(\frac{y-c_y}{x-c_x}\right)\right) & x-c_x \neq 0 \\ (y-c_y)\sin\theta & x-c_x = 0 \end{cases} \quad (16)$$

We now describe various modifications we have developed to the general framework for the fast analysis of VE-ASL data for the imaging of blood flow. For example, the vessel locations can be determined a priori from an image taken at the planning stage of the acquisition. However, there may be subsequent motion that results in a shift of the arteries from their expected location. In the next section we describe different approaches to overcome this problem, along with the other problems discussed above. Described below are new approaches in which, instead of directly inferring global parameters, such as artery locations, we may infer or estimate one or more global parameters to the encoding of one or more vessels in a region of interest. This may include, for example, inferring or estimating a rigid body transformation, reducing the number of degrees-of-freedom in the analysis.

Methods

Analysis

A non-limiting exemplary selection of analyses employing our modifications are now presented to examine the trade-off in accuracy and robustness offered by the use of differing constraints, in particular the application of estimations of one or more global parameters such as artery location, speed of flow, etc., in the analysis of VE-ASL data. These include:

Standard matrix inversion (MI) where the artery locations from a planning angiographic acquisition are used to form the encoding matrix according to equations (14) and (15), assuming flow speed was 30 cm/s in each artery. The encoding matrix was (pseudo) inverted and used to calculate voxelwise flow contributions. In the case of simulated data, MI using the true artery locations and flow speeds was also calculated (Mlt)

'Bayesian inversion' (BI): Bayesian analysis using fixed global parameters. In an embodiment, this includes estimation of flow contributions using equation (12) assuming equal class proportions and using the artery locations from the planning acquisition to define the encoding matrix according to equations (14) and (15) with, for example, flow speed 30 cm/s in each artery. This avoids the computationally costly estimation of 'global' parameters using equation (11) altogether.

Bayesian inference of artery locations (Bxy): In an embodiment, this includes maximum a posteriori (MAP) solution of equation (11) with the encoding matrix parameterised by the locations of the arteries in the encoding plane, according to equations (14) and (15). A prior was placed on the artery locations:

$$Pr([x_j, y_j]^T) \sim N(x_j; x_{0j}, 1) N(y_j; y_{0j}, 1) \quad (17)$$

where $x_{0j}$ and $y_{0j}$ are the estimates for the j th artery from, for example, a planning angiographic acquisition in mm. Estimation of flow contributions was then carried out using equation (12). In the case of simulated data, flow contributions using the MCMC solution of equation (9) was also calculated ($Bxy_{MCMC}$) for comparison.

In a further embodiment, rigid body transformation of artery locations was applied, for example using Bayesian inference of the locations and assuming a 3 DOF transformation (BT3). This represents a simple model of patient movement after planning. The transformation can be described by a rotation, $\theta$, and a 2D translation $[x_d \; y_d]^T$:

$$\begin{bmatrix} x_j \\ y_j \end{bmatrix} = \begin{bmatrix} \cos\theta & \sin\theta \\ -\sin\theta & \cos\theta \end{bmatrix} \begin{bmatrix} x_{0j} \\ y_{0j} \end{bmatrix} + \begin{bmatrix} x_d \\ y_d \end{bmatrix} \quad (18)$$

where the transformation was performed about the centre of the artery locations. Informative priors were applied to the transformation parameters:

$$Pr([x_d, y_d]^T) \sim N(x_d; 0, 1 \text{ mm}^2) N(y_d; 0, 1 \text{ mm}^2)$$

$$Pr(\theta) \sim N(0, (5°)^2) \quad (19)$$

Transformation parameters and class proportions were inferred using a MAP procedure via equation (11), and estimation of flow contributions was then carried out using equation (12).

In an embodiment, Bayesian inference of rigid body transformation and artery flow speeds (BT3v) was applied. This is the same as BT3 above but with the artery flow speeds, in equation (14), being inferred as extra variables with prior:

$$Pr(v_j) \sim N(30 \text{ cm/s}, (10 \text{ cm/s})^2) \quad (20)$$

In another embodiment, Bayesian inference of rigid body transformation assuming a 6 DOF 2-dimensional affine transformation (BT6). This is similar to BT3 above but with the entries in the rotation matrix being inferred:

$$\begin{bmatrix} x_j \\ y_j \end{bmatrix} = \begin{bmatrix} a & b \\ c & d \end{bmatrix} \begin{bmatrix} x_{0j} \\ y_{0j} \end{bmatrix} + \begin{bmatrix} x_d \\ y_d \end{bmatrix} \quad (21)$$

with priors on the rotation matrix entries:

$$Pr(a) \sim N(1, 0.1), Pr(b) \sim N(0, 0.1) Pr(c) \sim N(0, 0.1) Pr(d) \sim N(1, 0.1) \quad (22)$$

This extends the BT3 solution to a higher number of degrees-of-freedom to account for non-planar subject motion between planning and VE-ASL acquisition.

Analysis was performed in Matlab (MathWorks, Natick, Mass.) using code written in-house and was executed as a complied run time on an Intel Xeon Quad core server running at 3.0 GHz (all code was single threaded). MAP estimation of 'global' parameters was made using the BFGS Quasi-Newton method (Broyden, 1970; Fletcher, 1970; Goldfarb, 1970; Shanno, 1970) with a cubic line search (fminunc using the 'Medium scale' algorithm). To aid convergence of the inference to the global solution a multi-step evaluation was performed. Firstly vessel locations or transformation parameters were inferred with the class proportions fixed. Subsequently the class proportions were inferred with other parameters fixed, before a final stage where both class proportions and vessel locations or transformation parameters were inferred. For BT3v a further step was added at the end where the artery flow speeds were also inferred.

Simulations

To test the relative accuracy of the various modifications presented herein simulated data were generated that approximated a VE-ASL angiographic acquisition. The present modifications, however, are not limited to angiographic acquisition. They can also be applied to perfusion, for example. The simulation included 4 arteries in the labelling plane placed at the corners of a square (±10 mm in x and y).

Figure 2:
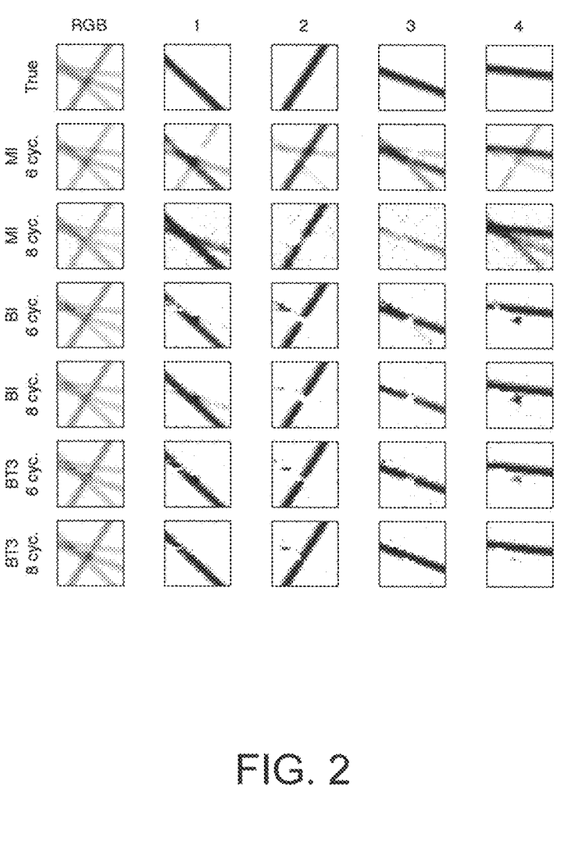
FIG. 2 depicts example flow images from the analysis of one set of simulated data.

These were treated as the locations obtained from a planning acquisition. For data generation these were subject to a two dimensional 3 DOF rigid body transformation with two translations and one rotation drawn randomly from a zero mean normal distribution with a standard deviation of 1 mm for translation and 1° for rotation. Additionally the flow speed in each artery was drawn from a normal distribution with mean 30 cm/s and standard deviation 5 cm/s (hard thresholds were applied for flow speeds exceeding 80 cm/s or falling below 3 cm/s). An imaging region 25×25×1 voxels was populated with four arterial segments whose centre and orientation was randomly generated, an example is shown in FIG. 2.

Data were generated from 8 encoding cycles detailed in Table 1, these represent a tag all, control all, two left-right, two anterior-posterior and two oblique encodings. The first 6 encoding cycles match the experimental design used in the real data (below). The final two oblique encoding cycles produce data for which the encoding matrix is full rank. Thus matrix inversion analysis is not underdetermined.

The parameters of the encoding cycles were based on the planning locations of the vessels prior to rigid body transformation to mimic a real experiment. 100 datasets were generated with both 6 and 8 cycles with each measurement being subject to white noise with an SNR of 10:1 relative to the signal magnitude of the labelled blood. Data were analysed according to the methods outlined above. The root-mean-square-error (RMSE) between the estimated flow contributions from each artery and the true values was calculated. Since it is the detection of vessels in the brain and discrimination of the contributions from the labelled arteries that is typically of clinical interest, receiver operating characteristics (ROC) curves were also generated from the simulated data. This was achieved by taking the estimated flow contribution images and using a threshold to create a binary image representing the presence or absence of artery segments. Over a range of threshold values rates of true and false flow identification were used to calculate the ROC curves. Table 1 provides the setup of the vessel-encoded cycles used to generate simulated data.

TABLE 1

| Cycle | $(c_x, c_y)$ | θ° | D |
|---|---|---|---|
| 1 | | Tag all | |
| 2 | | Control all | |
| 3 | (0, 0) | 0 | 10 |
| 4 | (20, 0) | 0 | 10 |
| 5 | (0, 0) | 270 | 10 |
| 6 | (0, 20) | 270 | 10 |
| 7 | (20, 20) | 135 | 4.47 |
| 8 | (20, 20) | 135 | 4.47 |

Real Data

Two sets of VE-ASL dynamic angiographic data were considered to illustrate the present methods. Data had been acquired at 3 T using a Siemens TIM Trio system (Siemens Healthcare Erlangen, Germany) under a technical development protocol agreed with local ethics and institutional committees. The first subject was a young healthy volunteer with no known neurologic deficit. The second subject was a patient with severe bilateral vertebral artery stenoses scanned according to a protocol approved by the local ethics review board.

Prior to VE-ASL acquisition a standard time-of-flight (TOF), or planning acquisition, image was acquired of the head and neck. This image was used to estimate the locations of the arteries within the labelling plane and set up the modulations used within the VE-ASL acquisition itself. Acquisition was performed using the vessel-encoded pseudo-continuous ASL method of Wong (Wong, 2007), followed closely by a two-dimensional thick-slab dynamic angiographic readout, as described in (Okell et al., 2010). Labelling was achieved by a pulse train of 1 sec duration using Gaussian pulses with an effective flip angle of 20°, 600 μsec duration and 960 μsec separation. 20 time points were acquired with a temporal resolution of 55 ms, allowing visualisation of the dynamics of the blood flow, using a segmented look-locker sampling strategy (Günther et al., 2001) with an excitation flip angle of 10°, 20 readout blocks with 3 phase encoding steps per readout block. Other readout parameters were: field-of-view 205×154 mm, matrix size 192×144, slab thickness 5 cm, total imaging time 10 minutes. The relatively long labelling duration used in this method means that the major cerebral vessels are filled with labelled blood at the first time point in the data, with subsequent time points showing outflow of the blood. Labelling was performed approximately 8 cm below the Circle of Willis where the two internal carotid and two vertebral arteries run approximately perpendicular to the transverse plane. Six VE-ASL cycles were performed: tag all, control all, tag left arteries whilst controlling right; tag right arteries whilst controlling left; tag anterior arteries (internal carotids) whilst controlling posterior; and tag posterior arteries (vertebrals) whilst controlling anterior.

Analysis was performed using the methods outlined above with the estimated artery locations from the TOF acquisition. The full complex magnitude and phase of the data was used for analysis, since substantial changes in the phase of signal from large vessels are possible, leading to artefacts in magnitude only data. For the methods where 'global' parameter estimation was required, the estimation was carried out on only the first time point image from within the dataset. This considerably reduced the size of the data to be processed and thus the computational cost. We used the first frame since it would contain the largest signal, as the ASL label still fills the major arteries at this stage. Flow parameter estimation was carried out using the full 20 time point data. The computation time for the parameter inference phase for each of the methods was recorded to give an indication of the relative speed of the different approaches.

Results

Simulated Data

FIG. 2 shows RGB and individual artery contribution images from one set of simulated data. Top row shows the true flow contributions from the four arteries within the imaging region used to generate the data. Results are shown from data generated with six or eight encoding cycles for analysis using matrix inversion (MI), 'Bayesian inversion' (BI) and Bayesian inference of a 3 DOF transformation (BT3). The left-most column shows the combined contributions from all four arteries using the RGB colour space (artery 1=magenta, 2=purple, 3=red, 4=green), the right four columns show the individual artery contributions. This set was chosen since it contained an area of overlap of multiple arteries in the imaging plane. Estimated images are shown from both six and eight cycle data for MI, BI and BT3 analyses with two arteries per class (APC), the other Bayesian methods produced images that were not visually distinguishable from BT3 in this case. The rank deficiency of the six cycle data was noticeable with MI, where there was substantial mixing between the different flow images. This was markedly reduced for the 8 cycle data. However, some mixing was still visible, a result of errors due to the movement of the vessel locations from their positions assumed for the calculation of the encoding matrix. Separation was good for all the Bayesian methods, the main source of separation errors occurring where three or more arteries overlapped.

Figure 3:
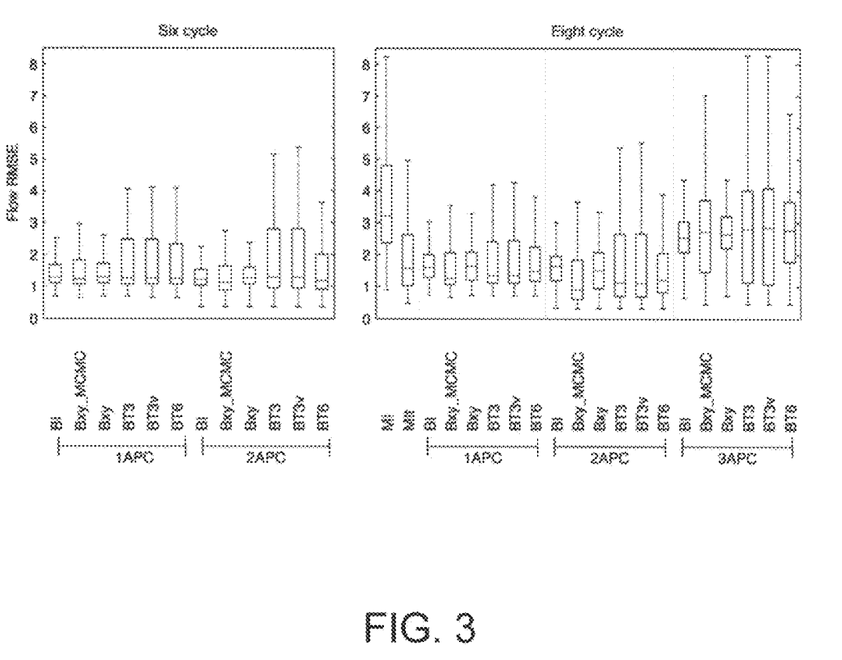
FIG. 3 illustrates the root-mean-squared error (RMSE) between flow images and true flow contributions across the simulated datasets for the various analysis methods considered for both six and eight cycles of vessel-encoding. Mlt for 6 cycles is not shown on these axes due to it having a median RMSE of 11.1.
Figure 4:
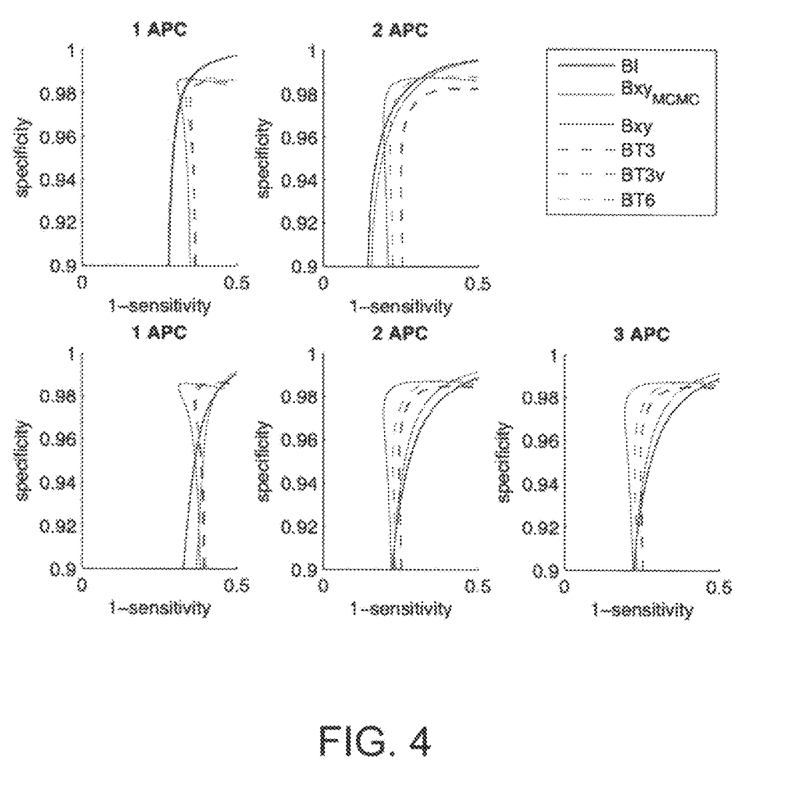
FIG. 4 depicts ROC curves for the identification of arteries from the simulated data: 6 cycle (upper) and 8 cycle (lower) data.

FIG. 3 shows the root-mean-squared error (RMSE) between flow images and true flow contributions across the simulated datasets for the various analysis methods considered for both six and eight cycles of vessel-encoding. Mlt for 6 cycles is not shown on these axes due to it having a median RMSE of 11.1. FIG. 4 shows the ROC curves for the estimated flow contributions across all the simulated datasets for the analysis methods considered. Median error across the different datasets was smallest using 2 arteries per class (APC), although the difference was marginal for the data containing six cycles. Smaller errors were observed when the data contained the full eight cycles specified in Table 1. There was negligible difference in the error between the BT3 and BT3v cases and these offered a small improvement over the BT6 and Bxy alternatives. The smallest error and greatest discrimination was achieved using the MCMC rather than MAP solution ($Bxy_{MCMC}$), although the improvement over a MAP solution was relatively small. Bayesian inversion (BI), while resulting in larger errors than the 'global' parameter search methods, still offered a marked improvement over standard matrix inversion analysis. Even when matrix inversion was performed using the true artery locations (Mlt) the Bayesian inversion (using the 'ideal' locations) was comparable if not better.

Healthy Subject Data

Figure 5:
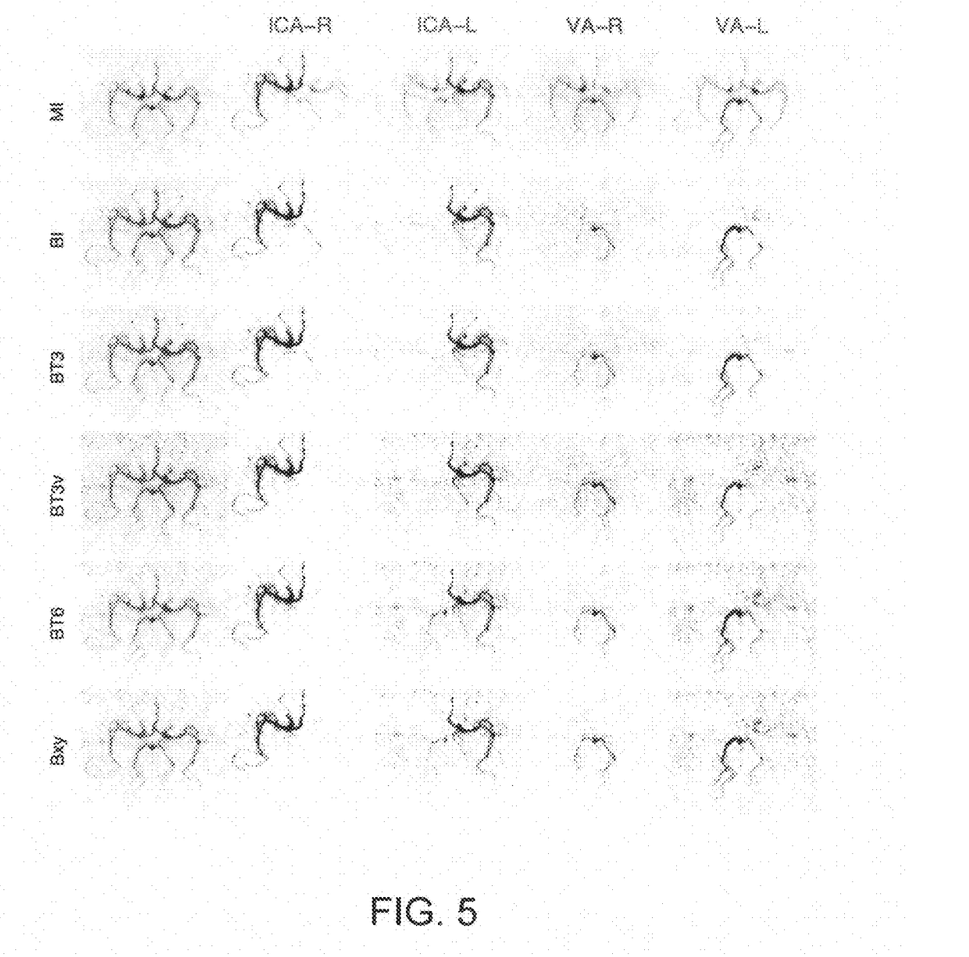
FIG. 5 depicts RGB flow image from a healthy subject: only the first frame from the dynamic angiographic acquisition of the Circle of Willis in the transverse view is shown.

FIG. 5 shows the first frame from the healthy subject dataset analysed using the general framework with 2 APC. Combined (left-most) and individual artery contributions from internal carotid arteries (ICA) and vertebral arteries (VA) are shown. All the Bayesian analysis methods showed a broadly similar flow image, but with some variation in the posterior artery segments. The matrix inversion (MI) solution produced poor separation due to the rank deficiency of the encoding matrix, the dominant artery in a vascular segment was generally correct, but artefactual contributions from all other arteries were seen almost everywhere.

The five different Bayesian analyses in FIG. 5 were broadly similar, although some differences can be seen in the posterior cerebral arteries. In general, the posterior cerebral artery territories are fed by the two vertebral arteries that fuse (in this case below the imaging region) to form the basilar artery, in which the vertebral blood may mix. It was apparent from all the methods that this mixed vertebral supply was present in the right posterior cerebral artery (PCA). It also appeared that the left PCA was being supplied by a combination of the mixed vertebral supply and flow from the left internal carotid artery (ICA) via the left posterior communicating artery (PCoA). Some contribution to the right PCA from the left ICA was seen for the BT6 and Bxy methods, this was considered likely to be an artefact since there was unlikely to be enough pressure to force blood from the left PCoA back along the proximal left PCA into the right PCA. Table 2 provides the computation times for 'global' parameter estimation (s) for the various Bayesian methods on the healthy dataset.

TABLE 2

|  | 1 APC | 2 APC |
|---|---|---|
| BT3 | 117.8 | 207.1 |
| BT3v | 520.2 | 545.7 |
| BT6 | 143.6 | 373.1 |
| Bxy | 380.3 | 201.9 |

Patient Data

Figure 6:
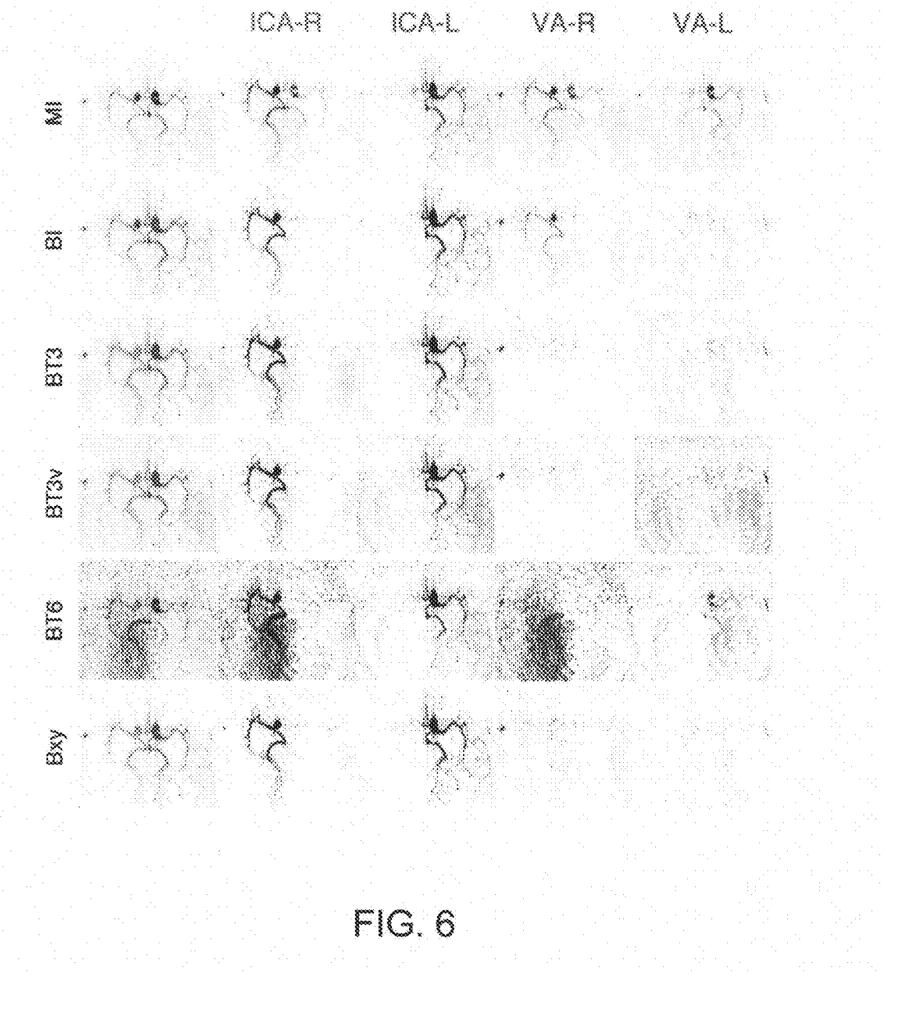
FIG. 6 depicts RGB flow images from a patient showing no flow contributions from the vertebral arteries.

FIG. 6 shows the first frame from the patient dataset analysed using the general framework. Combined (left-most) and individual artery contributions from internal carotid arteries (ICA) and vertebral arteries (VA) are shown. Effects of patient motion seen in the BI analysis are removed in the other methods; some artefactual appearance of the background noise can be seen in the BT6 results. In this case there was no apparent contribution from either vertebral, consistent with their clinical assessment. The posterior territories were being supplied via collateral flow from the ICAs through the PCoAs. This was evident from all the analysis methods based on the general framework, but as in the healthy subject, the separation was poor with MI. The BI method showed some contribution to the right cerebral arteries from the right vertebral. This appeared to be artefactual, primarily because the right vertebral 'contribution' very closely matched that of the right internal carotid. This artefact would be consistent with movement of the patient between planning and acquisition and the BT3 method reported a shift in the artery locations about their isocentre of 1.5 mm right, 3.2 mm anterior with 2.2° of rotation. The BT6 solution exhibited an increased contribution from background noise that was spread between the right carotid and vertebral components. In all the images a component from the right vertebral (red) could be seen on the right of the patient, this was identified as a branch of the right external carotid. It is likely that the right external carotid was labelled in a similar manner to the right vertebral due to its location in labelling plane.

DISCUSSION & CONCLUSIONS

Thus, we have shown the present systems and methods providing modification of the general framework for VE-ASL analysis are suitable for fast analysis of VE-ASL images. This permits non-invasive visualisation of vessels, such as arteries, for example in the brain, allowing each vessel's signal contribution to be separately determined. To avoid the computationally costly MCMC evaluation of 'global' parameters in the original solution for VE-ASL imaging we have developed systems and methods for fast analysis of VE-ASL imaging data in which we change the way one or more parameters to the encoding of the location of one or more blood vessels in a region of interest are determined.

Figure 7:
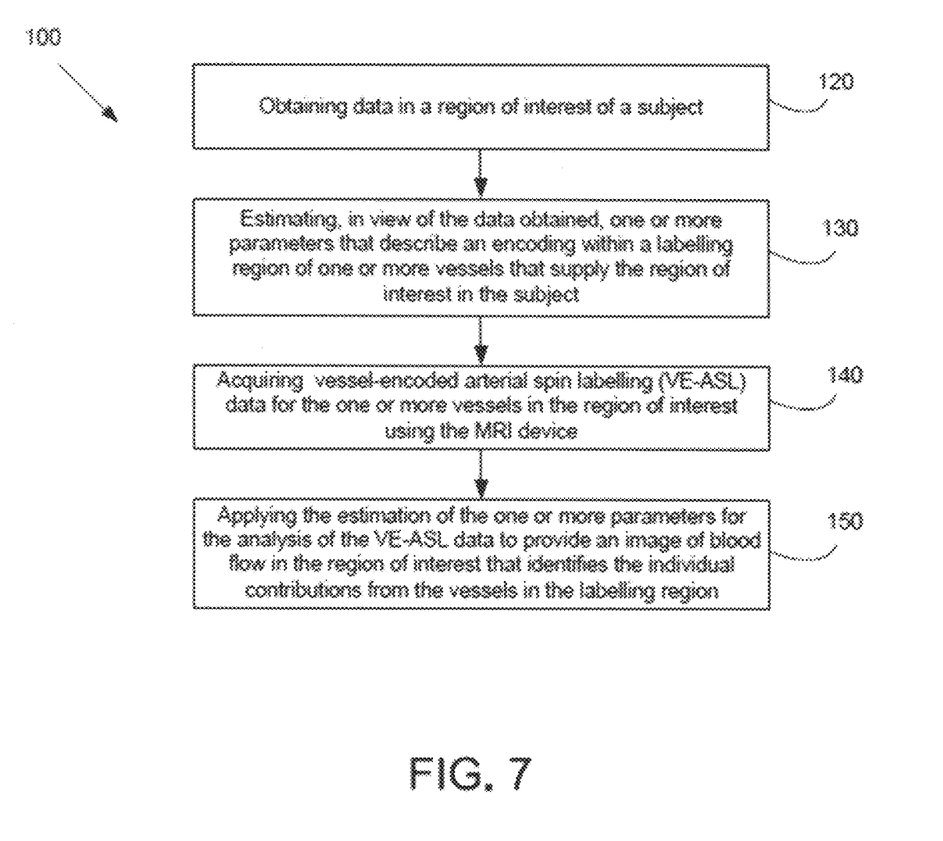
FIG. 7 depicts a non-limiting flow chart for one embodiment of our present fast analysis method for non-invasive imaging of blood flow using vessel-encoded arterial spin labelling (VE-ASL).

As depicted in the flow chart of FIG. 7, a non-limiting embodiment of our present fast analysis method for non-invasive imaging of blood flow using vessel-encoded materials spin labelling (VE-ASL) 100 includes obtaining data in a region of interest in a subject 120. The data may be obtained by any one or more acquisition methods. For example, the data may be obtained by one or more planning process acquisitions. A planning process acquisition may be used in planning a subsequent VE-ASL acquisition. A planning acquisition may be conducted, or data may be used from a previously conducted acquisition. The data may be obtained, for example, by providing a magnetic resonance imaging (MRI) device, positioning the subject in association with the MRI device, and using the MRI device to obtain the blood flow data. The data may be obtained in real-time or off-line from use of the MRI device. In various aspects we may use a time-of-flight (TOF) angiography sequence, which shows the major vessels such as arteries, as a planning acquisition to localise the vessels or arteries before performing the vessel-encoded scan to acquire the VE-ASL data. These vessel locations may then be used as priors for the analysis. Other angiographic images may also be used, such as phase-contrast angiography. The data obtained may be re-used in the analysis of the VE-ASL data. The data obtained may include vessel locations, speed of blood flow, off-resonance effects within the modulation function of the MRI device and/or vessel class proportions.

One or more parameters that describe an encoding within a labelling region of one or more vessels that supply the region of interest in the subject are estimated 130 in view of the obtained data in the region of interest. The estimation may be made or determined from the obtained. The one or more parameters may include, for example, a global set of estimated vessel locations, such as locations of arteries, in the region of interest. They may also include speed of flow, off resonance effects within the modulation function of the MRI device, and/or vessel class proportions.

We acquire VE-ASL data for the one or more vessels in the region of interest 140. The VE-ASL data may include angiographic data or perfusion data. This may be done by, for example, positioning a subject in association with an MRI device and using the MRI device to acquire the VE-ASL data. The estimation of the one or more parameters for the analysis of the VE-ASL data is applied for the analysis of the VE-ASL data to provide an image of blood flow in the region of interest that may identify the individual contributions of blood flow from the vessels in the labelling region 150. We may further determine from the blood flow in the one or more vessels within the region of interest an estimate of the flow contributions from those vessels to a selected voxel of interest.

In one or more embodiments we may apply the use of a fast solution to marginalize the posterior distribution to find and apply point estimates for one or more global parameters. As an example, we may apply maximum a posteriori (MAP) estimation. This coupled with only evaluating the global parameters on a single frame of the dynamic sequence, leads to more acceptable processing time for high-resolution angiographic data. Typically processing times when performing MAP estimation of 'global' parameters up to 600 seconds were observed for the real data considered. For comparison a similar MCMC analysis would take of the order of 40,000 seconds on the same hardware. The actual time taken will vary in practice from dataset to dataset because an iterative optimization procedure is involved.

A MAP estimation of the 'global' parameters provided satisfactory results within a clinically acceptable time frame. A possible disadvantage of this over the MCMC solution we have taken previously is that information about the uncertainty in the 'global' parameters is lost. However, the uncertainty associated with the 'global' parameters in this application is not critical. A point estimate that can be used to recover flow images from individual arteries may ameliorate this disadvantage. Another potential disadvantage is that a MAP method is more liable to find a local rather than the global minimum when compared with MCMC approaches. We might expect the posterior to possess multiple local minima because of the cyclic nature of the modulation functions. It is feasible that there would thus be multiple solutions for the vessel locations that result in very similar flow images. In practice the relatively informative priors used should avert this danger. Additionally the 'global' parameter values are not of direct interest (they can be considered nuisance parameters): it is the flow images that are desired. Thus as long as the flow image is correct, whether the estimated vessel locations match the true values or a cyclic equivalent is not an issue.

In one or more embodiments we may estimate or calculate 'global' parameters within a mask defined from the tag-control difference signal, including only voxels containing substantial blood flow, across all time frames. Since this typically contains fewer voxels processing time is faster and by using all time frames it would be less sensitive to late arriving blood as might occur in stenotic or occlusive vascular diseases.

In embodiments, to improve robustness in a clinical context we may modify the original general framework, reducing the number of free parameters associated with the artery locations in the labelling plane. This may be achieved by using the artery locations from a planning acquisition, and then modelling transformations that might be expected due to subject motion. In simulation and real data this was shown to confer some improvement in accuracy, although the overall effect was relatively small. However, in some clinical cases there may be an advantage to being able to more closely define the relative locations of the arteries as achieved using the exemplary transformations in the BT3 and BT6 solutions. For example, in the patient case there is complete occlusion of the vertebral arteries leading to no signal from these in the resulting images. There is a danger that the Bxy algorithm might shift the vertebral locations to the location of a peripheral vessel that has been unintentionally included in the labelling region. In such circumstances it becomes harder to determine unambiguously from the results that no signal arises from the missing vertebrals, since it may be simply that a stronger signal has been observed from the peripheral vessel. By fixing the relative locations of the arteries it is possible to interpret the zero signal from the vertebrals with greater confidence, but still allow for patient movement.

In embodiments, we have shown that it is possible to avoid MAP parameter estimation altogether by calculating flow images from Equation (12) using the assumed artery locations and equal class proportions from a planning acquisition. In terms of assuming known artery locations, this approach is similar to the matrix inversion approach, which uses a pseudo inversion of the encoding matrix. However, the MAP approach, which we have termed 'Bayesian inversion', also exploits the advantages of the classification built into the general framework, resulting in more accurate flow images, particularly in the face of a rank deficient encoding matrix. The reliance on accurate vessel locations means that BI is not most suitable when there has been motion between planning and acquisition, as seen in the patient dataset. However, it still shows a remarkable degree of robustness to artery location inaccuracy as demonstrated by the simulated data. Given the modest increase in computational complexity over matrix pseudo inversion we propose that BI is a natural replacement for MI analysis in cases where images must be produced rapidly following the acquisition.

Thus, data that has been acquired with the aid of a planning process image of the labelling region (region of interest) can also be used to provide satisfactory estimation. This image can be used to define the encoding cycles to achieve maximum labelling efficiency and allowing the artery locations to be estimated. It may be desirable to have a planning free acquisition, for example using randomly defined encoding cycles as proposed by (Guo and Wong, 2010). In this case the vessel locations would be unknown and so a Bxy analysis would most likely be called for.

Figure 8:
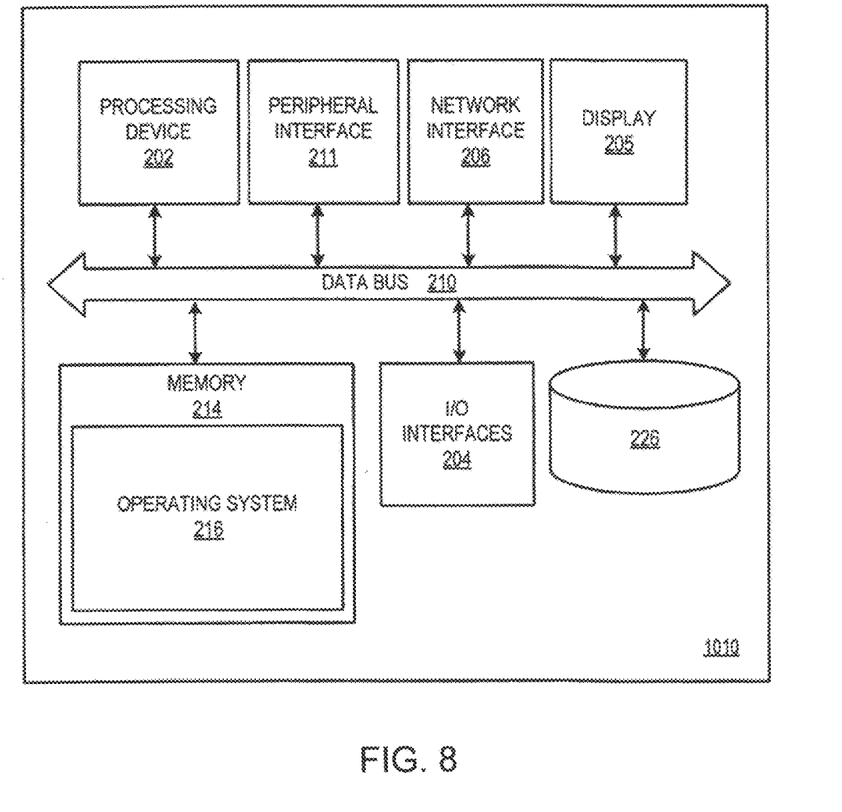
FIG. 8 is a schematic block diagram of an apparatus in which embodiments for providing a fast analysis method for non-invasive imaging of blood flow using vessel-encoded arterial spin labelling angiography disclosed herein may be implemented.

Reference is now made to FIG. 8, which depicts an apparatus 1010 in which the embodiments of systems and methods for providing a fast analysis method for non-invasive imaging of blood flow using vessel-encoded arterial spin labelling (VE-ASL) described herein may be implemented. The apparatus 1010 may be embodied in any one of a wide variety of wired and/or wireless computing devices, multiprocessor computing device, and so forth. As shown in FIG. 8, the apparatus 1010 comprises memory 214, a processing device 202, a number of input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the systems and methods for performing multi-parametric magnetic resonance diagnosis of liver disease described herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

Input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, or other display device.

In the context of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 8, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices (not shown) via the network interface 206 over a network 118. The apparatus 1010 may further comprise mass storage 226. The peripheral 211 interface supports various interfaces including, but not limited to IEEE-1394 High Performance Serial Bus (Firewire), USB, a serial connection, and a parallel connection. The apparatus 1010 shown in FIG. 8 may be embodied, for example, as a magnetic resonance apparatus, which includes a processing module or logic for performing conditional data processing, and may be implemented either off-line or directly in a magnetic resonance apparatus. For such embodiments, the apparatus 1010 may be implemented as a multi-channel, multi-coil system with advanced parallel image processing capabilities, and direct implementation makes it possible to generate immediate T1 maps available for viewing immediately after image acquisition, thereby allowing re-acquisition on-the-spot if necessary. Examples of apparatus in which the present systems and methods may be implemented are described in U.S. Pat. No. 5,993,398 and U.S. Pat. No. 6,245,027 and U.S. Publication No. 2011/0181285, which are incorporated by reference as if fully set forth herein.

The flow chart of FIG. 7 shows an example of functionality that may be implemented in the apparatus 1010 of FIG. 8. If embodied in software, each block shown in FIG. 7 may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 8) in a computer system or other system. The machine code may be converted from the source code, etc. If embodied in hardware, each block may represent a circuit or a number of interconnected circuits to implement the specified logical function(s).

Although the flow chart of FIG. 7 shows a specific order of execution, it is understood that the order of execution may differ from that which is depicted. For example, the order of execution of two or more blocks may be scrambled relative to the order shown. Also, two or more blocks shown in succession in FIG. 7 may be executed concurrently or with partial concurrence. Further, in some embodiments, one or more of the blocks shown in FIG. 7 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

It should be emphasized that the above-described embodiments are merely examples of possible implementations. Other methods for providing a fast analysis method for non-invasive imaging of blood flow in individual cerebral arteries using vessel-encoded arterial spin labelling angiography described herein may be used. Many variations and modifications may be made to the above-described embodiments without departing from the principles of the present disclosure. All such modifications and variations are intended to be included herein within the scope of this disclosure and protected by the following claims.

REFERENCES

Alsop, D. C., Detre, J. A., 1996. Reduced transit-time sensitivity in noninvasive magnetic resonance imaging of human cerebral blood flow. J. Cereb. Blood Flow Metab. 16, 1236-1249.

Broyden, C., 1970. The convergence of a class of double-rank minimization algorithms. IMA Journal of Applied Mathematics 6, 222.

Buxton, R., Frank, L., Wong, E., Siewert, B., Warach, S., Edelman, R., 1998. A general kinetic model for quantitative perfusion imaging with arterial spin labelling. Magnetic Resonance in Medicine 40, 383-396.

Chappell, M. A., Okell, T. W., Jezzard, P., Woolrich, M. W., 2010. A General Framework for the Analysis of Vessel Encoded Arterial Spin Labelling for Vascular Territory Mapping. Magnetic Resonance in Medicine 64, 1529-1539.

Dai, W., Robson, P. M., Shankaranarayanan, A., Alsop, D. C., 2010. Modified pulsed continuous arterial spin labelling for labelling of a single artery. Magn. Reson. Med. 64, 975-982.

Davies, N. P., Jezzard, P., 2003. Selective arterial spin labelling (SASL): perfusion territory mapping of selected feeding arteries tagged using two-dimensional radiofrequency pulses. Magn. Reson. Med. 49, 1133-1142.

Edelman, R. R., Siewert, B., Adamis, M., Gaa, J., Laub, G., Wielopolski, P., 1994. Signal targeting with alternating radiofrequency (STAR) sequences: application to MR angiography. Magn Reson Med 31, 233-238.

Fletcher, R., 1970. A new approach to variable metric algorithms. Computer Journal 13, 317-322.

Goldfarb, D., 1970. A Family of Variable-Metric Methods Derived by Variational Means. Mathematics of Computation 24, 23-26.

Gunther, M., 2006. Efficient Visualisation of vascular territories in the human brain by cycled arterial spin labelling MRI. Magnetic Resonance in Medicine 56, 671-675.

Gunther, M., Bock, M., Schad, L. R., 2001. Arterial spin labelling in combination with a look-locker sampling strategy: inflow turbo-sampling EPI-FAIR (ITS-FAIR). Magn Reson Med 46, 974-984.

Guo, J., Wong, E. C., 2010. From optimized Vessel Encoded PCASL (opt-VEPCASL) to randomly-encoded VEPCASL (re-VEPCASL). Proc. International Society of Magnetic Resonance in Medicine 18, 4096.

Helle, M., Norris, D. G., Rufer, S., Alfke, K., Jansen, O., van Osch, M. J. P., 2010a. Superselective pseudocontinuous arterial spin labelling. Magnetic Resonance in Medicine 64, 777-786.

Helle, M., Rufer, S., Alfke, K., Jansen, O., Norris, D. G., 2010b. Perfusion territory imaging of intracranial branching arteries—optimization of continuous artery-selective spin labelling (CASSL). NMR Biomed.

Hendrikse, J., van der Grond, J., Lu, H., van Zijl, P. C. M., Golay, X., 2004. Flow territory mapping of the cerebral arteries with regional perfusion MRI. Stroke 35, 882-887.

Lee, P. M., 1997. Bayesian Statistics: An introduction.

Mackay, D., 1995. Probable Networks and plausible predictions—A review of practical Bayesian methods for supervised neural networks. Network: Computation in Neural Systems 6, 469-505.

Okell, T. W., Chappell, M. A., Woolrich, M. W., Guenther, M., Feinberg, D. A., Jezzard, P., 2010. Vessel-Encoded Dynamic Magnetic Resonance Angiography Using Arterial Spin Labelling. Magnetic Resonance in Medicine 64, 698-706.

Shanno, D., 1970. Conditioning of Quasi-Newton Methods for Function Minimization. Mathematics of Computation 24, 647-656.

Wang, S. J., Nishimura, D. G., Macovski, A., 1991. Multiple-readout selective inversion recovery angiography. Magn Reson Med 17, 244-251.

Wong, E., 2007. Vessel-Encoded Arterial Spin-Labelling Using Pseudocontinuous Tagging. Magnetic Resonance in Medicine 58, 1086-1091.

Wong, E. C., Cronin, M., Wu, W.-C., Inglis, B., Frank, L. R., Liu, T. T., 2006. Velocity-selective arterial spin labelling. Magn. Reson. Med. 55, 1334-1341.

Zimine, I., Petersen, E. T., Golay, X., 2006. Dual vessel arterial spin labelling scheme for regional perfusion imaging. Magn. Reson. Med. 56, 1140-1144.

What is claimed:

1. A method for analysis of vessel-encoded arterial spin labelling (VE-ASL) data, comprising:
   A. Obtaining data for a region of interest in a subject;
   B. Estimating, in view of the data obtained, one or more parameters that describe an encoding within a labelling region of one or more vessels that supply the region of interest in the subject;
   C. Acquiring vessel-encoded arterial spin labelling (VE-ASL) data for the one or more vessels in the region of interest; and
   D. Applying the estimation of the one or more parameters for the analysis of the VE-ASL data to provide an image of blood flow in the region of interest that identifies the individual contributions from the vessels in the labelling region.

2. The method of claim 1, further comprising determining from the blood flow of the one or more vessels within the region of interest an estimate of the flow contributions from those vessels to a selected voxel of interest.

3. The method of claim 1, wherein the one or more parameters includes one or more vessel locations.

4. The method of claim 1, wherein the one or more parameters further includes one or more of, speed of flow, off resonance effects or vessel class proportions.

5. The method of claim 1, wherein the data is obtained as a part of a planning process acquisition and the one or more parameters are derived from data from the planning process acquisition to provide an estimate of the vessel locations within the labelling region.

6. The method of claim 5, wherein the one or more parameters represent a relationship between the true vessel locations in the region of interest and the vessel locations estimated from the planning process acquisition.

7. The method of claim 1, wherein the estimation is derived from a marginalized a posteriori distribution of the VE-ASL data within the region of interest to derive point estimates of the location of the one or more vessels.

8. The method of claim 7, wherein the estimation is derived from a maximum a posteriori (MAP) optimization.

9. The method of claim 1, wherein the analysis is applicable to all types of vessel encoded arterial spin labelling (VE-ASL) data acquisitions.

10. The method of claim 1, further including the steps of providing a magnetic resonance imaging (MRI) device, positioning the subject in association with the MRI device, and using the MRI device to obtain the vessel-encoded blood flow data and acquire the vessel-encoded arterial spin labelling (VE-ASL) data.

11. A system, comprising
at least one computing device;
at least one application executable in the at least one computing device, the at least one application comprising logic that:
  A. obtains data for a region of interest in a subject;
  B. estimates, in view of the data obtained, one or more parameters that describe an encoding within a labelling region of one or more vessels that supply the region of interest in the subject;
  C. acquires vessel-encoded arterial spin labelling (VE-ASL) data for the one or more vessels in the region of interest; and
  D. applies the estimation of the one or more parameters for the analysis of the VE-ASL data to provide an image of blood flow in the region of interest that identifies the individual contributions from the vessels in the labelling region.

12. The system of claim 11, further comprising logic that determines from the blood flow of the one or more vessels within the region of interest an estimate of the flow contributions from those vessels to a selected voxel of interest.

13. The system of claim 11, wherein the one or more parameters includes one or more vessel locations.

14. The system of claim 11, wherein the one or more parameters further includes one or more of, speed of flow, off resonance effects or vessel class proportions.

15. The system of claim 11, wherein the data is obtained as a part of a planning process acquisition and the one or more parameters are derived from data from the planning process acquisition to provide an estimate of the vessel locations within the labelling region.

16. The system of claim 15, wherein the one or more parameters represent a relationship between the true vessel locations in the region of interest and the vessel locations estimated from the planning process acquisition.

17. The system of claim 11, wherein the estimation is derived from a marginalized a posteriori distribution of the VE-ASL data within the region of interest to derive point estimates of the location of the one or more vessels.

18. The system of claim 17, wherein the estimation is derived from a maximum a posteriori (MAP) optimization.

19. The system of claim 11, wherein the analysis is applicable to all types of vessel encoded arterial spin labelling (VE-ASL) data acquisitions.

20. The method of claim 1, wherein, the estimating of step (B) includes inferring or estimating a rigid body transformation, thereby reducing the number of degrees-of-freedom of the analysis.

* * * * *